United States Patent [19]

Neirinckx et al.

[11] 4,406,877

[45] Sep. 27, 1983

[54] $^{82}$RB GENERATING METHOD AND ELUENT

[75] Inventors: Rudi D. Neirinckx, East Windsor; Michael D. Loberg, Princeton, both of N.J.

[73] Assignee: E. R. Squibb & Sons, Inc., Princeton, N.J.

[21] Appl. No.: 156,285

[22] Filed: Jun. 4, 1980

[51] Int. Cl.$^3$ ...................... A61K 43/00; A61K 49/00

[52] U.S. Cl. .......................................... 424/1.1; 423/2

[58] Field of Search ................................ 423/2; 424/1

[56] References Cited

U.S. PATENT DOCUMENTS

| | | | |
|---|---|---|---|
| 3,183,152 | 5/1965 | Szekely et al. | 424/78 |
| 3,240,709 | 3/1966 | Rankin | 424/329 |
| 3,333,919 | 8/1967 | Buckingham | 423/2 |
| 3,664,964 | 5/1972 | Haney et al. | 252/364 |
| 3,882,036 | 5/1975 | Krezanoski et al. | 252/106 |
| 3,903,297 | 9/1975 | Robert | 424/318 |
| 3,953,567 | 4/1976 | Grant et al. | 423/2 |
| 4,057,618 | 11/1977 | Salmon et al. | 424/1 |
| 4,064,227 | 12/1977 | Brown et al. | 424/1 |
| 4,067,959 | 1/1978 | Bolz | 424/1 |
| 4,276,267 | 6/1981 | Bentley et al. | 423/2 |

OTHER PUBLICATIONS

Kopecky et al., Int. J. Appl. Rad. Isotopes, 25 (1974) 469–470.

Grant et al., J. Nucl. Med., 16(4) 300–304 (1975).

Yano et al., J. Nuclear Med., vol. 9, No. 7, 412–415, 1974.

Yano et al., J. Nucl. Med., vol. 18, No. 1, 46–50, 1977.

Grant et al., J. Nucl. Med., vol. 19, No. 11, 1250–1255, 1978.

Yano et al., Int. J. Appl. Rad. Isotopes, 30:382–385, 1979.

Yano et al., J. Nucl. Med., vol. 20, No. 9, 961–966, 1979.

Kolprathipanja et al., Int. J. Appl. Rad. Isotopes, 30:447–449, 1979.

Budinger et al., J. Nucl. Med., vol. 16, No. 5, 429–431, 1975.

Krizek et al., J. Nucl. Med., 18:609, 1977.

Budinger et al., J. Nucl. Med., 20:603, 1979.

Neirinckx et al., Second Int. Symposium on Radio Pharmaceutical Chem., MRC, Oxford, 1978, p. 109.

*Primary Examiner*—Christine M. Nucker
*Attorney, Agent, or Firm*—Lawrence S. Levinson

[57] ABSTRACT

The present invention provides a low $^{82}$Sr breakthrough eluent and method of generating $^{82}$Rb from $^{82}$Sr from a $^{82}$Sr charged inorganic adsorbant column. Eluting is done with a pharmaceutically acceptable saline and buffer solution, which is preferably isotonic $^{82}$Sr breakthroughs of $10^{-8}$ are obtained at clinically useful elution rates greater than 10 ml per minute. Phosphate and carbonate buffers are preferred. $Al_2O_3$ and $ZrO_2$ are preferred inorganic radiation damage resistant adsorbants.

12 Claims, No Drawings

$^{82}$RB GENERATING METHOD AND ELUENT

BACKGROUND OF THE INVENTION

Rubidium —82, a positron emitter with a half-life of 75-sec is readily obtainable from the parent Sr-82 ($T_{\frac{1}{2}}$=25 days). Rubidium can be used as a diffusible flow tracer for the myocardium and kidney, and as a nondiffusible tracer for brain blood flow. Serial injections of Rb-82 can be administered every 5 to 10 minutes by eluting (milking) Rb-82 from its 25-day Sr-82 parent. The advantages of Rb-82 are low radiation dose, ability to provide for repeated examinations every 5 minutes without constraints from body background, and a convenient and economical supply of a short-half-life positron emitter. (Yano et al, The Journal of Nuclear Medicine 20:961-966, 1979.)

Significant quantities of $^{82}$Sr are available for clinical investigation. The short-lived daughter, 75-second $^{82}$Rb, is of value in biomedicine for circulation and perfusion studies as well as for myocardial imaging as mentioned in U.S. Pat. No. 3,953,567.

Grant et al disclose partial resolution of inconsistencies in the medical literature regarding the performance characteristics of $^{82}$Sr/$^{82}$Rb radionuclide generators as discussed at page 1250 of Grant el al, The Journal of Nuclear Medicine, Vol. 19, Number 11; pages 1250-1254, 1978.

Yano et al, Journal of Nuclear Medicine, 18:46-50, 1977 disclose that two different ion-exchange resins loaded with spallation-produced $^{82}$Sr indicated that the Bio-Rex 70 Saline system was superior to the Chelex-100 $NH_4Cl$—$NH_4OH$ system for the separation of $^{82}$Rb. Not only was the observed separation factor higher with Bio-Rex 70 resin, but a 2% saline solutin was also observed to be a better eluent for intravenous infusion than the 0.1 M $NH_4OH$—$NH_4Cl$ buffer.

Yano et al in the International Journal of Applied Radiation & Isotopes, Vol. 30, pages 382-385, 1979, disclose breakthrough data for $^{85}$Sr batch studies with $Al_2O_3$ adsorber using 2% NaCl, pH 8-9 eluent; Bio-Rex 70 adsorber using 2% NaCl, pH 8-9 eluent; and Chelex 100 adsorber using 0.1 M ($NH_4Cl+NH_4OH$), pH 9 eluent. Yano et al cite previous work with Bio-Rex 70, a weakly acidic cation resin and Chelex 100, a chelating ion exchange resin, which indicated that a good separation of $^{82}$Rb from $^{82}$Sr could be obrained; however, the former ion exchange resin exhibits an increase in $^{82}$Sr breakthrough after a moderate number of elutions with 2% NaCl at pH 7-8, while the latter resin requires an $NH_4OH+NH_4Cl$ buffer at pH 9.0 as the eluent solution which is not desirable for intravenous infusion.

Rubidium and potassium are chemically related elements and are in the alkali-metals group of the periodic table. The biological behavior of Rb and K is very similar, both being taken up by muscle. Furthermore the myocardial uptake of Rb after intravenous infusion is related to the rate of blood flow through the myocardium. $^{84}$Rb, a positron-emitting isotope, has been used with coincidence gamma-ray counters to determine coronary blood flow in man. However, because of its relatively long half-life of 33 days and its high cost, $^{84}$Rb presents disadvantages for coronary blood-flow studies. $^{82}$Rb has physical characteristics that are suitable for visualizing deep-lying organs. It has a half-life of 75 sec and decays 96% of the time by positron emission with a maximum energy of 3.15 Mev. The positron is accompanied by a 0.77-Mev gamma ray (9.0% abundant) to the ground state of $^{82}$Kr. Its very short half-life offers low radiation exposure and the possibility of quick repeat studies. Because it is a positron emitter, the positron scintillatin camera, with its high sensitivity and excellent image-forming characteristics for deep-lying organs can be used; see Yano et al, Journal of Nuclear Medicine, volume 9, Number 7 pages 412-415; 1968.

$^{82}$Rb is produced continuously by decay of the parent isotope, $^{82}$Sr which decays with a half-life of 25 days. By use of a chromatographic column, $^{82}$Rb can be milked from the parent isotope every 5-10 , minutes.

SUMMARY OF THE INVENTION

The present invention provides a low $^{82}$Sr breakthrough eluent and method of separating $^{82}$Rb from a $^{82}$Sr charged inorganic adsorbant column. Eluting is done with a pharmaceutically acceptable saline and buffer solution, which is preferably isotonic. $^{82}$Sr breakthroughs of $10^{-8}$/ml are obtained at clinically useful elution rates greater than 10 ml. per minute. Phosphate and carbonate buffers are preferred. $Al_2O_3$ and $ZrO_2$ are preferred inorganic radiation damage resistant adsorbants.

DETAILED DESCRIPTION OF THE INVENTION

The method and eluents of the present invention are useful in position imaging and quantitation of blood flow through the myocardium, brain and kidneys.

The present invention provides improved breakthrough characteristics. It has been discovered that breakthrough of Sr may be lowered by providing a pharmaceutically acceptable buffer in a pharmaceutically acceptable saline eluent.

an inorganic ion exchange adsorbant column is used because of good resistance to radiation damage. The eluents of the present invention are suitable for intravenous infusion.

Preferably the buffer is a phosphate salt or a carbonate salt. Most preferably the buffer is a phosphate salt.

Bacteriostats may be beneficially added to the eluent. Preferred bacteriostats are those which are pharmaceutically acceptable buffers, for example parabens.

The eluent may be buffered at a pharmaceutically acceptable pH. Preferably the pH is from 6.0 to pH 10. Most preferably the pH is from pH 7.5 to pH 9.5. the concentration of the buffer in the eluent preferably is from .01 mmol to 200 mmol per liter of eluent solution.

The saline concentration of the eluent is a pharmaceutically acceptable concentration. Preferably the saline is isotonic (0.9%).

A column containing inorganic adsorbant is charged with $^{82}$Sr. Preferably the inorganic adsorbant is $Al_2O_3$ or $ZrO_2$. the column is then eluted with the eluent. Preferably the column is eluted at greater than 10 ml per minute.

At clinically useful flow rates of about 50 ml per minute, $^{82}$Sr breakthrough of $10^{-8}$ per ml of eluent are obtained by the present invention. Breakthrough is the ratio of microcuries of $^{82}$Sr in the eluent to the microcuries of $^{82}$Sr in the adsorber.

Phosphate salts include alkali phosphates, alkaline earth phosphates, alkali metal hydrogen phosphates, alkaline earth hydrogen phosphates as well as hydrates of phosphate salts. Also phosphate salts include all phosphorous oxides which form phosphates upon addition to water.

A preferred phosphate salt is $Na_2HPO_4$ which may be added to the eluent as $Na_2HPO_4 \cdot 7H_2O$. In the saline eluent it forms $Na+$ and $PO_4{}^{-3} \rightleftarrows HPO_4{}^{-2} \rightleftarrows H_2PO_4{}^{\ominus}$. Upon addition of NaOH some of the $H_2PO_4{}^{\ominus}$ would be taken up in the formation of $HPO_4{}^{-2}$. The balanced equation being:

$$NaH_2PO_4 + NaOH \rightleftarrows Na_2HPO_4 + H_2O$$

When acid is added for example HCl; some $H_2PO_4{}^{\ominus}$ is formed. The balanced equation being:

$$Na_2HPO_4 + HCl \rightleftarrows NaH_2PO_4 + NaCl.$$

Carbonate salts include water soluble carbonate salts such as alkali metal carbonates and alkali metal hydrogen carbonates for example $NaHCO_3$. In water $NaHCO_3$ forms $Na+$ and $CO_3{}^{-2} \rightleftarrows H\ CO_3{}^{\ominus} \rightleftarrows H_2CO_3$. Upon addition of NaOH; $HCO_3{}^{-1}$ and $H_2CO_3$ are taken up and $CO_3{}^{-2}$ and $HCO_3{}^{-1}$ respectively are formed. Upon addition of HCl; $CO_3{}^{-2}$ and $HCO_3{}^{-}$ *are taken up and* $HCO_3{}^{-}$ *and* $H_2CO_3$ respectively are formed.

The buffer of the present invention controls the amount of $^{82}Sr$ breakthrough. Much lower $^{82}Sr$ breakthrough is obtained where the saline eluent is buffered than where saline alone in aqueous solution is used. Also where the column material is pre-equilibrated with the buffer solution reduced $^{82}Sr$ breakthrough is obtained. Examples 1 and 2 are specific embodiments of the invention.

EXAMPLE 1

A standard sized Minitec generator (commercially available from E. R. Squibb and Sons, Inc., Princeton, New Jersey) is used. The column is filled with $Al_2O_3$ (2 cc bed volume of Basic Woelm). The column is then pre-equilibrated by washing with 0.025% (dry weight) of $Na_2\ H\ PO_4 \ .\ 7\ H_2O$ aqueous isotonic saline solution. The column is loaded with 0.5 cc (500 micrograms) of a mixture of $^{82}Sr$, $^{85}Sr$ and $^{83}Rb$ in isotonic saline and sodium hydroxide solution having pH 12. 0.5 cc of air is pulled from the lower end of the column while loading the activity. The column is allowed to set for 2 hours for adsorbtion to take place. Then the column is eluted with 0.025% (dry weight) of $Na_2HPO_4 \ .\ 7H_2O$ aqueous isotonic saline solution.

EXAMPLE 2 the procedure of Example 1 is used except that autoclaving is carried out in this example.

Table 1 shows the breakthrough fraction per ml of eluent from the column used in Examples 1 and 2 and the pH of the eluate for the volume ranges of eluent shown. the elution speed is 50 ml/min.

TABLE I

| Volume (ml) | | Breakthrough fraction of $^{82}Sr$/ml; Example 1 | Breakthrough fraction of $^{82}Sr$/ml; Example 2 |
|---|---|---|---|
| 0-200 | ($^{83}Rb$ Elution) | $\leqq 4 \times 10^{-8}$ | $\leqq 4 \times 10^{-8}$ |
| 200-300 | 400 ml eluated at 50 ml/min. | | |
| 800-900 | | $\leqq 5 \times 10^{-8}$ | $\leqq 1.5 \times 10^{-8}$ |
| 1400-1500 | | $\leqq 10^{-8}$ | $\leqq 10^{-8}$ |
| 2000-2100 | | $\leqq 2 \times 10^{-8}$ | $\leqq 3 \times 10^{-8}$ |
| 2100-2200 | Columns rested 4 days then 1st eluate collected (1st) | $4 \times 10^{-7}$ | $10^{-6}$ |
| 2200-2300 | | $5 \times 10^{-8}$ | $1.4 \times 10^{-7}$ |
| 2800-2900 | | $\leqq 2 \times 10^{-8}$ | $\sim 5 \times 10^{-8}$ |
| 3400-3500 | | $< 3 \times 10^{-9}$ | $3 \times 10^{-8}$ |
| 4000-4100 | | $< 3 \times 10^{-9}$ | $1.5 \times 10^{-8}$ |
| 4600-4700 | | $\sim 6 \times 10^{-9}$ | $9 \times 10^{-8}$ |
| 5200-5300 | | $\sim 6 \times 10^{-9}$ | $1.1 \times 10^{-7}$ |
| 5800-5900 | | $< 3 \times 10^{-9}$ | $1.3 \times 10^{-7}$ |
| 6400-6500 | Blown dry and rested (rested 2 days) | $< 3 \times 10^{-9}$ | $1.5 \times 10^{-7}$ |
| 6500-6600 | Column rested 2 days | $2.5 \times 10^{-8}$ | $1.5 \times 10^{-7}$ |
| 6600-6700 | | $< 5 \times 10^{-9}$ | $5 \times 10^{-8}$ |
| 7200-7300 | | $2 \times 10^{-8}$ | $6 \times 10^{-8}$ |
| 7800-7900 | | $< 10^{-8}$ | $7 \times 10^{-8}$ |
| 7900-8000 | | $5 \times 10^{-8}$ | |

The procedure used in the examples is that the generator is eluted for 2 minutes at 50 ml per minute resulting in 100 ml of eluate. The 100 ml fraction is then counted on a Ge(Li) detector for 777 KeV $^{82}Rb$ gamma ray.

$2.2\mu$ Ci of $^{82}Sr$ is used as a comparative standad from which to calculate the activity of $^{82}Sr$ in the 100 ml eluate.

We claim:

1. A low $^{82}Sr$ breakthrough method of generating $^{82}Rb$ from a $^{82}Sr$ charged inorganic adsorbant column comprising eluting the $^{82}Rb$ from the said inorganic adsorbant with an eluent comprising a pharmaceutically acceptable saline and buffer solution.

2. The method of claim 1 wherein said inorganic adsorbant is $Al_2O_3$ or $ZrO_2$.

3. The method of claim 1 wherein said eluent comprises a phosphate salt or a carbonate salt and isotonic saline.

4. The method of claim 1 wherein said eluent solution is buffered at pH 6.0 to pH 10, said column is eluted at greater than 10 ml per minute, and said eluent solution is isotonic and acceptable for intravenous infusion.

5. the method of claim 4 wherein said eluent solution comprises a carbonate salt.

6. The method of claim 4 wherein said column is pre-equilibrated with a buffered isotonic saline solution.

7. The method of claim 1 wherein said eluent solution further comprises a bacteriostat.

8. A pharmaceutically acceptable solution comprising $^{82}Rb$, a saline solution and a buffer.

9. A pharmaceutically acceptable solution in accordance with claim 8 wherein the saline solution is isotonic.

10. A pharmaceutically acceptable solution in accordance with claim 8 further comprising a bacteriostat.

11. A pharmaceutically acceptable solution in accordance with claim 10 wherein the buffer and bacteriostat are a single ingredient.

12. A pharmaceutically acceptable solution in accordance with claim 8 wherein the buffer is a phosphate salt or a carbonate salt.

* * * * *

UNITED STATES PATENT AND TRADEMARK OFFICE
CERTIFICATE OF CORRECTION

PATENT NO. : 4,406,877

DATED : September 27, 1983

INVENTOR(S) : Rudi D. Neirinckx and Michael D. Loberg

It is certified that error appears in the above—identified patent and that said Letters Patent is hereby corrected as shown below:

Column 1, line 35, "solutin" should be --solution--.
Column 1, line 47, "obrained" should be --obtained--.
Column 2, line 4, "scintillatin" should be --scintillation--.
Column 2, line 36, "an" should be --An--.
Column 3, line 54, "the" should be --The--.
Column 3, line 59, "the" should be --The--.
Column 4, line 30, "standad" should be --standard--.
Column 4, line 48, "the" should be --The--.

Signed and Sealed this

*Twenty-ninth* Day of *November 1983*

[SEAL]

*Attest:*

GERALD J. MOSSINGHOFF

*Attesting Officer* *Commissioner of Patents and Trademarks*